United States Patent

Takama et al.

[11] Patent Number: 5,929,027
[45] Date of Patent: Jul. 27, 1999

[54] PHYSIOLOGICALLY ACTIVE POLYPEPTIDE-CONTAINING PHARMACEUTICAL COMPOSITION

[75] Inventors: Shigeyuki Takama, Kagawa-ken; Yukiko Inamoto, Takamatsu; Takahiko Wato, Kagawa-ken; Akiya Yamada, Takamatsu; Naoki Uchida; Misuzu Kadoriku, both of Kagawa-ken, all of Japan

[73] Assignee: Teikoku Seiyaku Kabushiki Kaisha, Kagawa-ken, Japan

[21] Appl. No.: 08/815,574

[22] Filed: Mar. 12, 1997

Related U.S. Application Data

[62] Division of application No. 08/262,362, Jun. 20, 1994, abandoned, which is a continuation of application No. 07/893,575, Jun. 4, 1992, abandoned.

[30] Foreign Application Priority Data

Jun. 7, 1991 [JP] Japan .................... 3-136462

[51] Int. Cl.⁶ .................................. A61K 38/00
[52] U.S. Cl. ................... 514/2; 514/14; 514/15; 514/16; 514/17; 530/307; 424/409; 424/420; 424/493; 424/502
[58] Field of Search .................... 514/2, 14–17; 424/409, 420, 493, 502

[56] References Cited

U.S. PATENT DOCUMENTS

| | | | |
|---|---|---|---|
| 4,211,769 | 7/1980 | Okada et al. | 424/177 |
| 4,397,951 | 8/1983 | Taki | 435/188 |
| 4,540,602 | 9/1985 | Motoyama | 427/213.31 |
| 4,603,044 | 7/1986 | Geho et al. | 424/9 |
| 4,871,723 | 10/1989 | Makino | 514/167 |
| 4,873,081 | 10/1989 | Ogiso | 424/81 |
| 4,952,560 | 8/1990 | Kigasawa et al. | 514/2 |
| 4,954,512 | 9/1990 | Oguro | 514/352 |
| 5,204,327 | 4/1993 | Kiyota | 514/12 |
| 5,320,853 | 6/1994 | Noda | 424/472 |
| 5,338,759 | 8/1994 | Shechter et al. | 514/492 |
| 5,350,741 | 9/1994 | Takada | 514/3 |
| 5,482,706 | 1/1996 | Igari | 424/85.7 |

FOREIGN PATENT DOCUMENTS 0302772  2/1989  European Pat. Off. .

OTHER PUBLICATIONS

World Patents Index Latest, Section Ch, Week 8708, Derwent Publication Ltd., London, GB, Class B, AN 87–053768.
Chemical Abstracts, vol. 109, No. 4, Jul. 25, 1998, Abstract No. 27629T, p. 304, Col. 1.
Patel, Biochem. Soc. Trans., (1989) 17(5) 931.
Gardner et al., Biochem. Soc. Trans., (1989) 17(5) 934–937.
Lee, Biochem. Soc. Trans., (1989) 17(5) 937–940.

*Primary Examiner*—Cecilia J. Tsang
*Assistant Examiner*—David Lukton
*Attorney, Agent, or Firm*—Birch, Stewart, Kolasch & Birch, LLP

[57] ABSTRACT

A pharmaceutical composition comprising a physiologically active polypeptide, an absorption promoting agent consisting of a combination of an organic acid and a fatty acid sucrose ester in admixture with a pharmaceutically acceptable carrier or diluent, which is suitable for oral administration and for application to the oral cavity, by which the polypeptide can sufficiently be absorbed through the intestinal tract or the mucous membrane in the oral cavity and exhibit the physiological activities without being suffered from enzymolysis.

5 Claims, 8 Drawing Sheets

PHYSIOLOGICALLY ACTIVE POLYPEPTIDE-CONTAINING PHARMACEUTICAL COMPOSITION

This application is a divisional of copending application Ser. No. 08/262,362, filed on Jun. 20, 1994 now abandoned, which was a 37 CFR § 1.62 continuation of Ser. No. 07/893,575, filed on Jun. 4, 1992 now abandoned, the entire contents of which are hereby incorporated by reference.

TECHNICAL FIELD OF THE INVENTION

This invention relates to a physiologically active polypeptide-containing pharmaceutical composition. More particularly, it relates to a composition suitable for oral administration or application to the oral cavity, which comprises a physiologically active polypeptide, an absorption promoting agent consisting of a combination of an organic acid and a fatty acid sucrose ester in admixture with a conventional pharmaceutically acceptable carrier or diluent.

PRIOR ART

Polypeptides such as insulin and calcitonin are water soluble high molecular weight compounds which are easily decomposed with stomach juice or intestine proteases (e.g. pepsin, trypsin), and hence, when these polypeptides are orally administered, they can not exhibit their physiological activities without being absorbed.

Accordingly, in order to exhibit the physiological activities, these polypetides are usually used in the form suitable for injection. However, such an administration form is not convenient and gives sometimes pain to the patients particularly when they must be administered at certain intervals or frequently.

From the above viewpoint, it has been investigated to use the polypeptides in other administration forms than injection, and the present inventors have proposed a pharmaceutical composition suitable for administration by a vaginal route (Japanese Patent First Publication (Kokai) No. 294632/1989). Pharmaceutical composition for oral administration has also been proposed, for example, compositions incorporated with fatty acid sucrose esters (cf. Japanese Patent First Publication (Kokai) Nos. 10020/1987 and 33128/1987), but these compositions are still not sufficient in absorbability of the active ingredient.

BRIEF DESCRIPTION OF THE INVENTION

According to the intensive studies by the present inventors, it has been found that by incorporating a combination of an organic acid and a fatty acid sucrose ester as an absorption promoting agent into the composition, the physiologically active polypeptide can effectively be absorbed via intestinal tract or mucous membrane in the oral cavity, and hence, the composition is useful for oral administration or for application to the oral cavity.

An object of the invention is to provide a physiologically active polypeptide-containing pharmaceutical composition which is suitable for oral administration or for application to the oral cavity. Another object of the invention is to promote the absorption of the physiologically active polypeptide through the intestinal tract or mucous membrane in the oral cavity by using a combination of an organic acid and a fatty acid sucrose ester as an absorption promoting agent. A further object of the invention is to provide a rapidly soluble composition suitable for application to the oral cavity. These and other objects and advantages of the invention will be apparent to those skilled in the art from the following description.

DETAILED DESCRIPTION OF THE INVENTION

Figure 1:
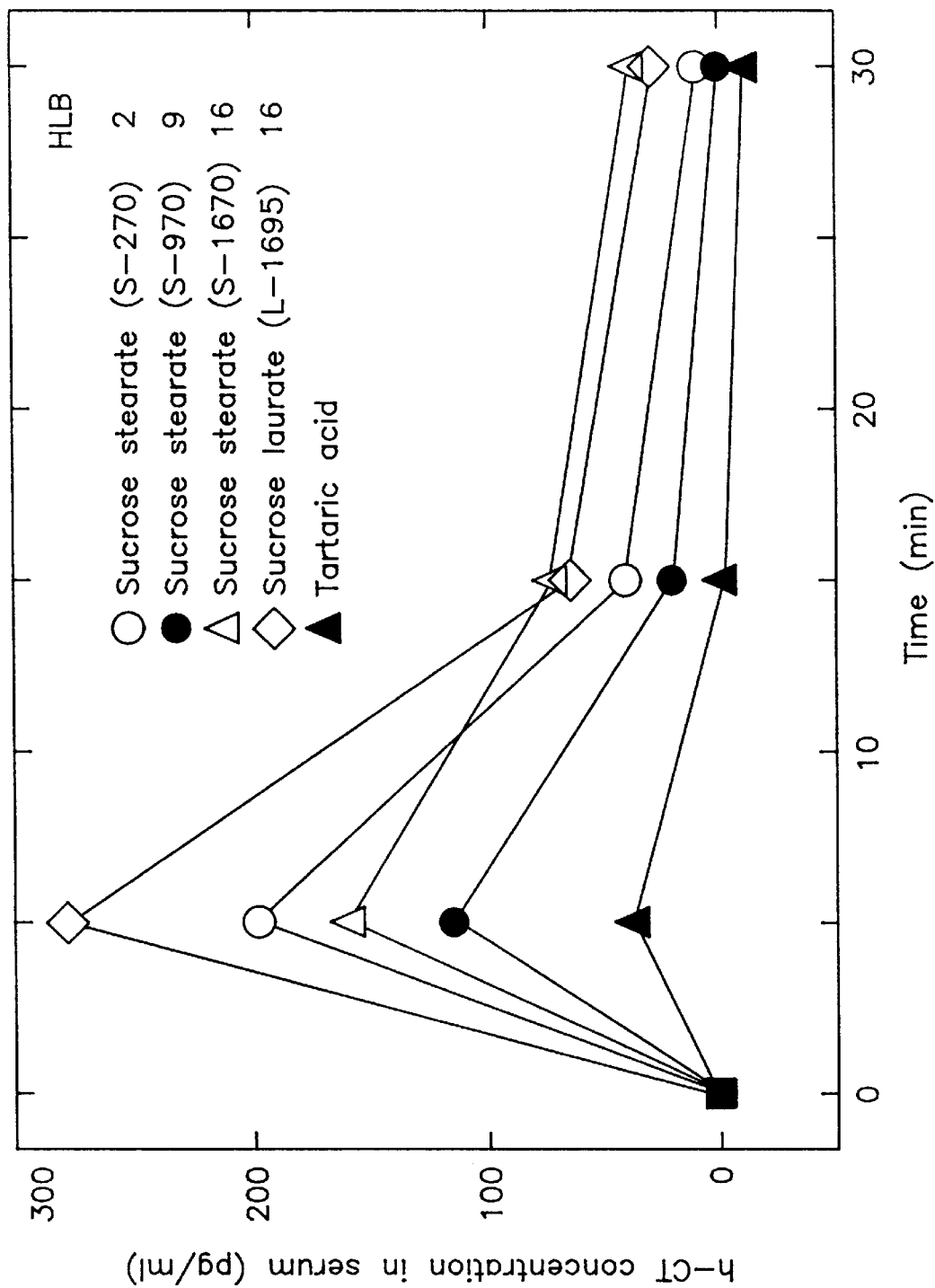
FIG. 1 is a graph showing the effects for promoting absorption of human calcitonin (h-CT) by a combination of various fatty acid sucrose esters and tartaric acid.

The physiologically active polypeptide-containing pharmaceutical composition of the invention comprises as an active ingredient an effective amount of a physiologically active polypeptide, an absorption promoting agent consisting of a combination of an organic acid and a fatty acid sucrose ester in admixture with the conventional pharmaceutically acceptable carrier or diluent, which is suitable for oral administration or for application to the oral cavity.

The organic acid used as one of the absorption promoting agent includes acetic acid, butyric acid, fumaric acid, malonic acid, phthalic acid, propionic acid, glutaric acid, adipic acid, valeric acid, caproic acid, maleic acid, ascorbic acid, isoascorbic acid, malic acid, succinic acid, lactic acid, tartaric acid, citric acid, and benzoic acid, among which the preferred ones are tartaric acid, citric acid, malic acid, lactic acid, benzoic acid and succinic acid. These organic acids may be used alone or in combination of two or more thereof. The amount of the organic acids may vary depending on the kinds of the preparation, but in case of a composition for oral administration, it is used in an amount of 0.1 to 70% by weight, preferably 1 to 50% by weight, based on the whole weight of the composition. In case of a composition suitable for application to the oral cavity (sublingual tablet), it is used in an amount of 0.1 to 30% by weight, preferably 2 to 20% by weight, based on the whole weight of the composition. Besides, in case of a rapidly soluble preparation for application to the oral cavity, it is used in an amount of 30 to 90% by weight, preferably 50 to 80% by weight, based on the whole weight of the preparation (in the lyophilized form).

The fatty acid sucrose ester includes sucrose stearate, sucrose palmitate, sucrose oleate, sucrose laurate, sucrose behenate, and sucrose erucate, among which the preferred ones are sucrose stearate, sucrose palmitate, sucrose oleate, and sucrose laurate. These fatty acid sucrose esters may be used alone or in combination of two or more thereof. The amount of the fatty acid sucrose esters may vary depending on the kinds of the preparation, but in case of a composition for oral administration, it is used in an amount of 0.1 to 50% by weight, preferably 0.5 to 30% by weight, based on the whole weight of the composition. In case of a composition suitable for application to the oral cavity (sublingual tablet), it is used in an amount of 0.1 to 20% by weight, preferably 1 to 10% by weight, based on the whole weight of the composition. Besides, in case of a rapidly soluble preparation for application to the oral cavity, it is used in an amount of 5 to 50% by weight, preferably 15 to 35% by weight, based on the whole weight of the preparation (in the lyophilized form).

The physiologically active polypeptides used in the invention are polypeptides having a comparatively low molecular weight. Suitable examples of the physiologically active polypeptides are, insulin, angiotensin, vasopressin, desmopressin, LH-RH (luteinizing hormone-releasing hormone), somatostatin, calcitonin, glucagon, oxytocin, gastrins, somatomedins, secretin, h-ANP (human atrial natriuretic peptide or factor), ACTH (adrenocorticotropic hormone), MSH (melanocyte-stimulating hormone), β-endorphin, muramyl dipeptide, enkephalins, neurotensin, bombesin, VIP (vasoactive intestinal polypeptide), CCK-8 (cholecystokin-8), PTH (parathyroid hormone), CGRP (calcitonin gene related peptide), TRH (thyrotropin releasing hormone), endothelin, TSH (thyroid-stimulating hormone), and their derivatives.

The polypetides used in the present invention include not only the naturally occurred polypeptides but also the physiologically active derivatives thereof. For instance, the calcitonins used in the present invention include not only the naturally occurred calcitonins such as salmon calcitonin, human calcitonin, porcine calcitonin, eel calcitonin, chicken calcitonin, rat calcitonin, bovine calcitonin, and sheep calcitonin, but also analogous products such as $[ASU^{1,7}]$-eel calcitonin, i.e. elcatonin.

The physiologically active polypeptides are contained in the composition of the present invention in an amount sufficiently exhibiting the activities, which may vary depending on the kinds of the polypeptides. For instance, in case of calcitonins, the content thereof is in an amount wherein the calcitonins can sufficiently exhibit their activities suitable for treating page 's disease, hypercalcemia and osteoporosis.

The composition of the present invention may optionally contain animal proteins and/or vegetable proteins in order to prevent any undesirable enzymolysis of the polypeptides during absorption after oral administration. The animal and vegetable proteins are preferably the conventional proteins suitable for foods and medicaments.

Preferred examples of the animal proteins are albumin (e.g. bovine serum albumin, human serum albumin, etc.), casein, gelatin, and the like. Preferred examples of the vegetable proteins are gluten, zein, soy bean protein, and the like. These animal and vegetable proteins may be used alone or in combination of an animal protein and a vegetable protein in an appropriate ratio. The amount of the animal and/or vegetable proteins to be incorporated into the composition of the present invention may vary depending on the kinds of the polypeptides to be stabilized, but is usually in the range of 0.001 to 25% by weight based on the whole weight of the composition.

The composition of the present invention includes various types of composition, i.e. compositions for oral administration, such as tablets, capsules, granules, etc., and compositions for application to the oral cavity, such as sublingual tablets. These compositions may be prepared in a conventional manner using the conventional carriers and diluents, such as excipients, binders, lubricants, etc.

The carriers used for tablets include excipients such as lactose, sucrose, glucose, starches, crystalline cellulose, etc. which are usually used in an amount of 50 to 90% by weight based on the whole weight of the composition; binders such as hydroxypropyl cellulose, carboxymethyl cellulose, carboxymethyl cellulose sodium, gum arabic, gelatin, polyvinyl alcohol, polyvinylpyrrolidone, tragacanth, sodium arginate, etc. which are usually used in an amount of 1 to 25% by weight based on the whole weight of the composition; lubricants such as magnesium stearate, calcium stearate, talc, etc. which are usually used in an amount of 0.5 to 3% by weight based on the whole weight of the composition.

The materials for the enteric coating includes hydroxypropyl methyl cellulose phthalate, hydroxypropyl methyl cellulose acetate succinate, cellulose acetate phthalate, methacrylic copolymer, and the like.

The carriers used for sublingual tablets include excipients such as lactose, sucrose, mannitol, sorbitol, starches, etc. which are usually used in an amount of 50 to 90% by weight based on the whole weight of the composition; binders such as crystalline cellulose, hydroxypropyl cellulose, carboxymethyl cellulose, hydroxypropyl methyl cellulose, methyl cellulose, dextrin, etc. which are usually used in an amount of 1 to 15% by weight based on the whole weight of the composition; disintegrators such as carboxymethyl cellulose calcium, low-substituted hydroxypropyl methyl cellulose, starches, etc. which are usually used in an amount of 1 to 15% by weight based on the whole weight of the composition; lubricants such as magnesium stearate, calcium stearate, talc, etc. which are usually used in an amount of 0.5 to 3% by weight based on the whole weight of the composition.

The composition for application to the oral cavity, particularly sublingual tablets, include a rapidly soluble composition which is rapidly dissolved within the oral cavity. The rapidly soluble composition is prepared by using one or more of the carriers such as gelatin, agar, polyvinylpyrrolidone, or natural gums (e.g. guar gum, locust bean gum, etc.) instead of excipients, binders and lubricants, and mixing homogeneously the active polypeptides and the absorption promoting agents to the carriers and then lyophilizing the mixture in a conventional manner.

The compositions of the present invention and the effects thereof are illustrated by the following Experiments and Examples but should not be construed to be limited thereto.

EXPERIMENT 1

Effects for promoting absorption of calcitonin by a combination of various organic acids and various fatty acid sucrose esters:

Solutions containing bovine serum albumin (BSA) 0.3 w/v %, an absorption promoting agent (a combination of various organic acids 0.5 and 1.0 w/v % and sucrose laurate 0.5 w/v %) and human calcitonin (h-CT) 5 μg/ml were prepared.

Male Wistar rats (weighing about 250 g) were anesthetized with Nembutal, and before administering the test solution (the calcitonin solution prepared above), the blood was collected from right external jugular vein. After subjecting the rats to ventrotomy, each calcitonin solution was administered to the lower part of the small intestine by a closed loop method in an amount of 0.1 ml per 100 g of rat. After the administration, the blood was collected at intervals (after 5, 15, 30 and 60 minutes). After the serum was separated, the calcium concentration in serum was measured with Calcium C kit (manufactured by Wako Junyaku K. K., Japan) (n=3). The results are shown in Table 1.

TABLE 1

[Lowering rate of serum calcium (%)]

| Oragnic acids | Concent- ration (%) | Time after administration (min) | | | |
|---|---|---|---|---|---|
| | | 5 | 15 | 30 | 60 |
| Malic acid | 0.5 | 1.5 | 5.0 | 8.8 | 4.8 |
| Succinic acid | 0.5 | 2.6 | 4.7 | 3.9 | −2.5 |
| Lactic acid | 0.5 | 1.9 | 7.6 | 9.0 | 4.4 |
| Tartaric acid | 0.5 | 3.9 | 5.3 | 5.2 | −2.8 |
| Tartaric acid | 1.0 | 0.4 | 8.2 | 9.9 | 10.1 |
| Citric acid | 1.0 | 0.1 | 4.1 | 6.1 | −2.8 |
| Benzoic acid | 1.0 | 2.9 | 10.8 | 10.1 | 8.3 |

As is shown in Table 1, in each test solution, the lowering of serum calcium was observed.

EXPERIMENT 2

Effects for promoting absorption of an active substance by using fatty acid sucrose esters having different HLB values:

Solutions containing BSA 0.3 w/v %, an absorption promoting agent (a combination of tartaric acid 1.0 w/v % and each of the following fatty acid sucrose esters 0.5 w/v %) and h-CT 10 μg/ml were prepared.

| | Fatty acid sucrose esters | HLB value |
|---|---|---|
| 1. | Sucrose stearate (S-270) | 2 |
| 2. | Sucrose stearate (S-970) | 9 |
| 3. | Sucrose stearate (S-1670) | 16 |
| 4. | Sucrose laurate (L-1695) | 16 |

As a reference solution, there was used a 0.1M acetate buffer solution containing BSA 0.3 w/v %, tartaric acid 1.0 w/v % and h-CT 10 μg/ml.

In the same manner as described in Experiment 1, the test solution was administered, and the blood was collected at intervals (after 5, 15, 30 and 60 minutes). After the serum was separated, the h-CT concentration in serum was measured by RIA. The results are shown in the accompanying FIG. 1, wherein the value is shown by the difference to the initial value.

As is shown in FIG. 1, the calcitonin solutions of the invention showed the h-CT concentration in blood became maximum 5 minutes after the administration and showed higher h-CT concentration in blood than that of the reference solution (using tartaric acid alone).

EXPERIMENT 3

Effects for promoting absorption of an active substance by using fatty acid sucrose esters having different fatty acid residues:

By using fatty acid sucrose esters having HLB 16 and different fatty acid residues, there were prepared solutions containing BSA 0.3 w/v %, an absorption promoting agent (a combination of tartaric acid 1.0 w/v % and each of the following fatty acid sucrose esters 0.5 w/v %) and h-CT 5 μg/ml.

| Fatty acid sucrose esters | Fatty acid residue |
|---|---|
| 1. Sucrose stearate (S-1670) | stearic acid |
| 2. Sucrose palmitate (S-1670) | palmitic acid |
| 3. Sucrose laurate (L-1695) | lauric acid |

In the same manner as described in Experiment 1, the test solution was administered to the rats, and the blood was collected at intervals and the calcium concentration in serum was measured likewise. The results are shown in the accompanying FIG. 2.

Figure 2:
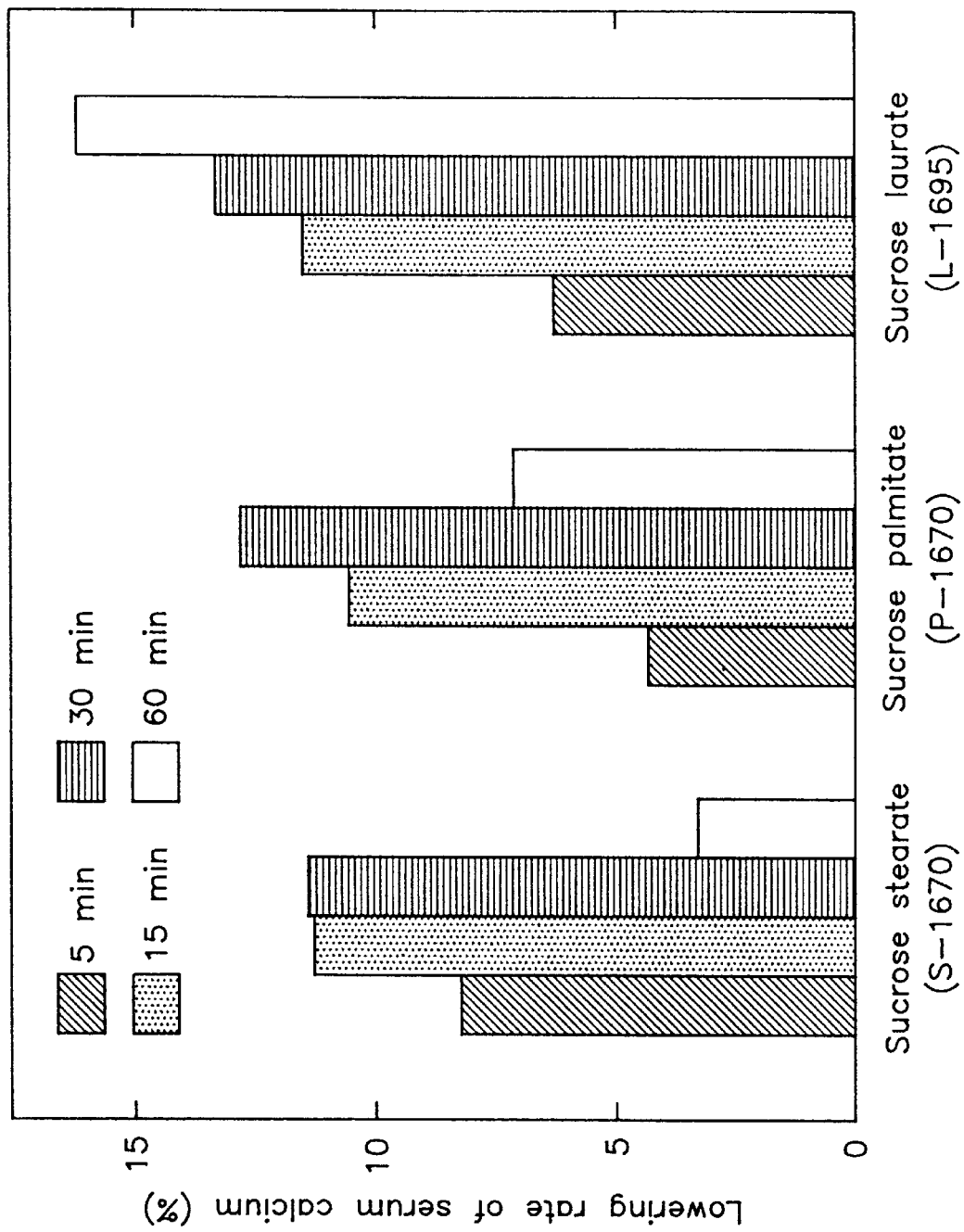
FIG. 2 is a graph showing the effects for lowering calcium in serum accompanied to the h-CT absorption promoting effects by a combination of various fatty acid sucrose esters and tartaric acid.

As is shown in FIG. 2, in all test solutions, there was observed lowering of blood calcium concentration while the fatty acid residue was different.

EXPERIMENT 4

Comparison of the effects for promoting absorption of an active substance between the use of tartaric acid or a fatty acid sucrose ester alone and the use of a combination thereof:

Solutions containing BSA 0.3 w/v %, an absorption promoting agent (a combination of tartaric acid 1.0 w/v % and sucrose laurate 0.5 w/v %) and h-CT 5 μg/ml and solutions containing BSA 0.3 w/v %, an absorption promoting agent (either alone of tartaric acid or sucrose laurate) and h-CT 5 μg/ml were prepared.

In the same manner as described in Experiment 1, the test solution was administered to the rats, and the blood was collected at intervals. After the serum was separated, the calcium concentration and h-CT concentration in serum were measured. The results are shown in the accompanying FIG. 3 and FIG. 4.

Figure 3:
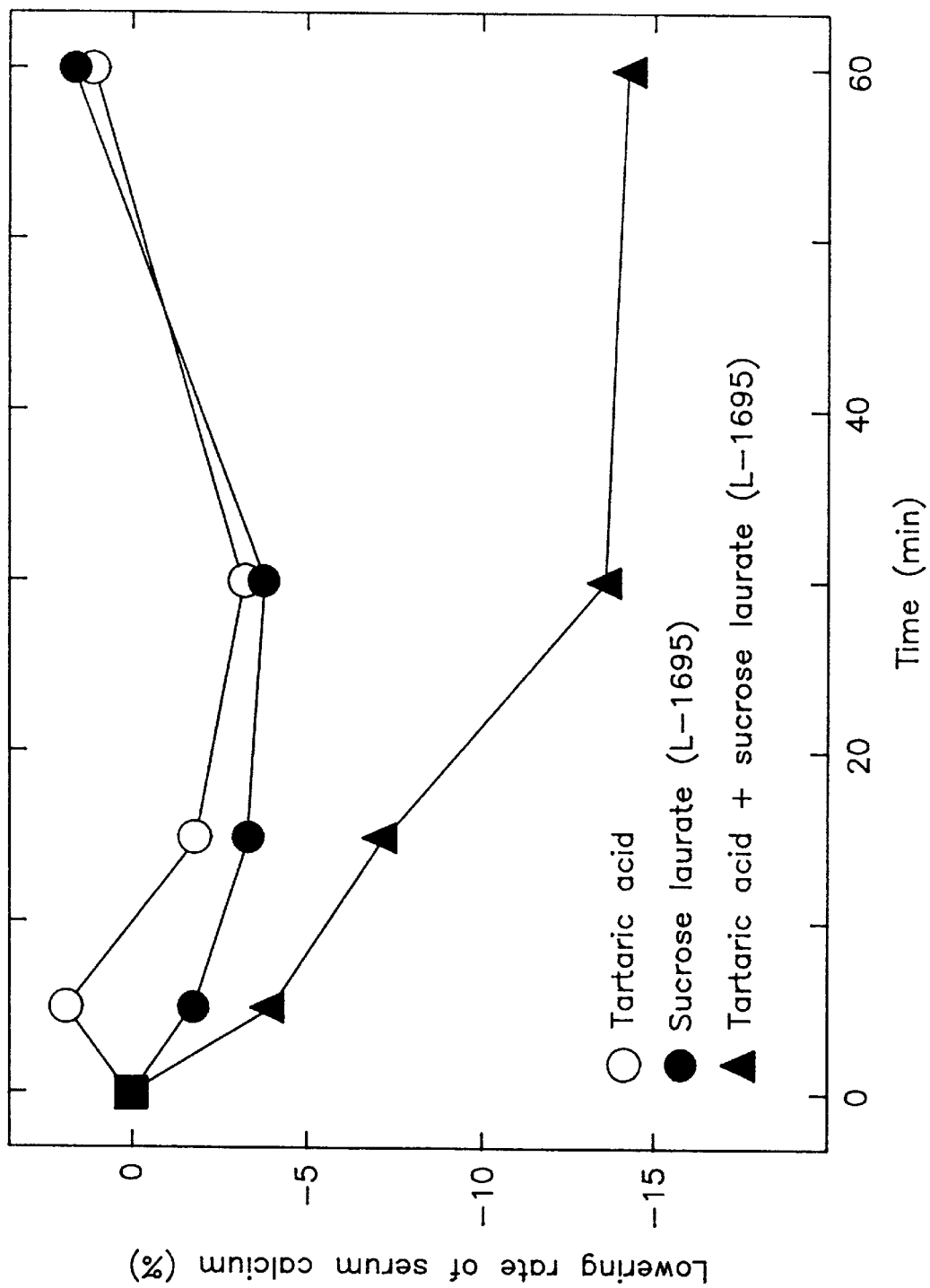
FIG. 3 is a graph showing comparison in the serum calcium lowering effects between the use of a combination of sucrose laurate and tartaric acid, and the use thereof alone.
Figure 4:
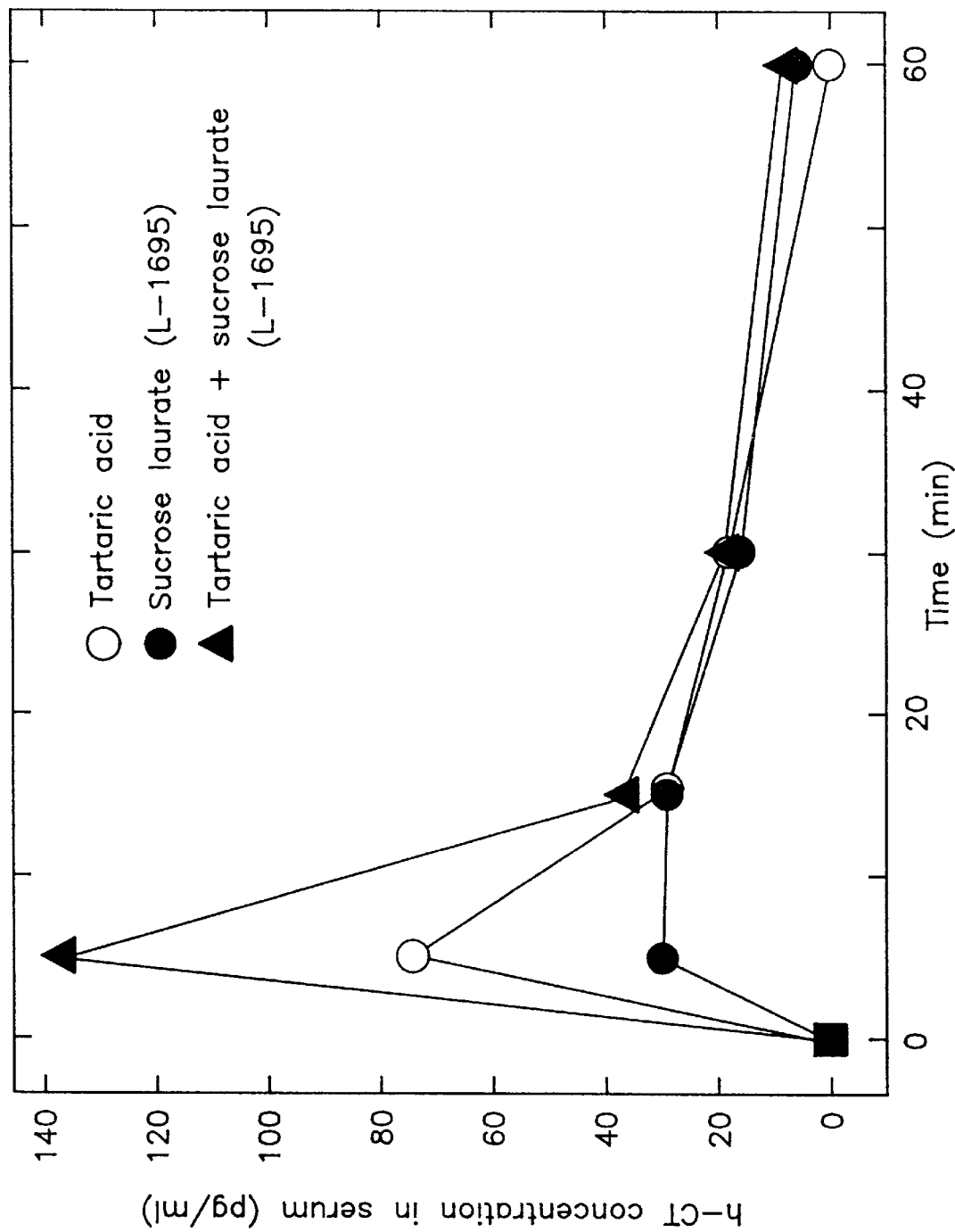
FIG. 4 is a graph showing comparison in the effects for promoting absorption of h-CT between the use of a combination of sucrose laurate and tartaric acid, and the use thereof alone.

As are shown in FIG. 3 and FIG. 4, in view of the lowering of the blood calcium concentration and the change of the h-CT concentration in blood, the absorption promoting agent consisting of a combination of tartaric acid and sucrose laurate showed superior effects for promoting absorption of h-CT in comparison with the use of tartaric acid or sucrose laurate alone.

EXPERIMENT 5

Effects for promoting absorption of TSH:

A solution containing BSA 0.3 w/v %, an absorption promoting agent (a combination of tartaric acid 1.0 w/v % and sucrose stearate (S-1670) 0.5 w/v %) and TSH 500 μg/ml was prepared. As a reference solution, there was prepared a solution containing BSA 0.3 w/v % and TSH 500 μg/ml.

In the same manner as described in Experiment 1, the test solution was administered to the rats in an amount of TSH 100 μg per each rat and the blood was collected at intervals. After the serum was separated, the blood TSH concentration was measured by RIA. The results are shown in the accompanying FIG. 5.

Figure 5:
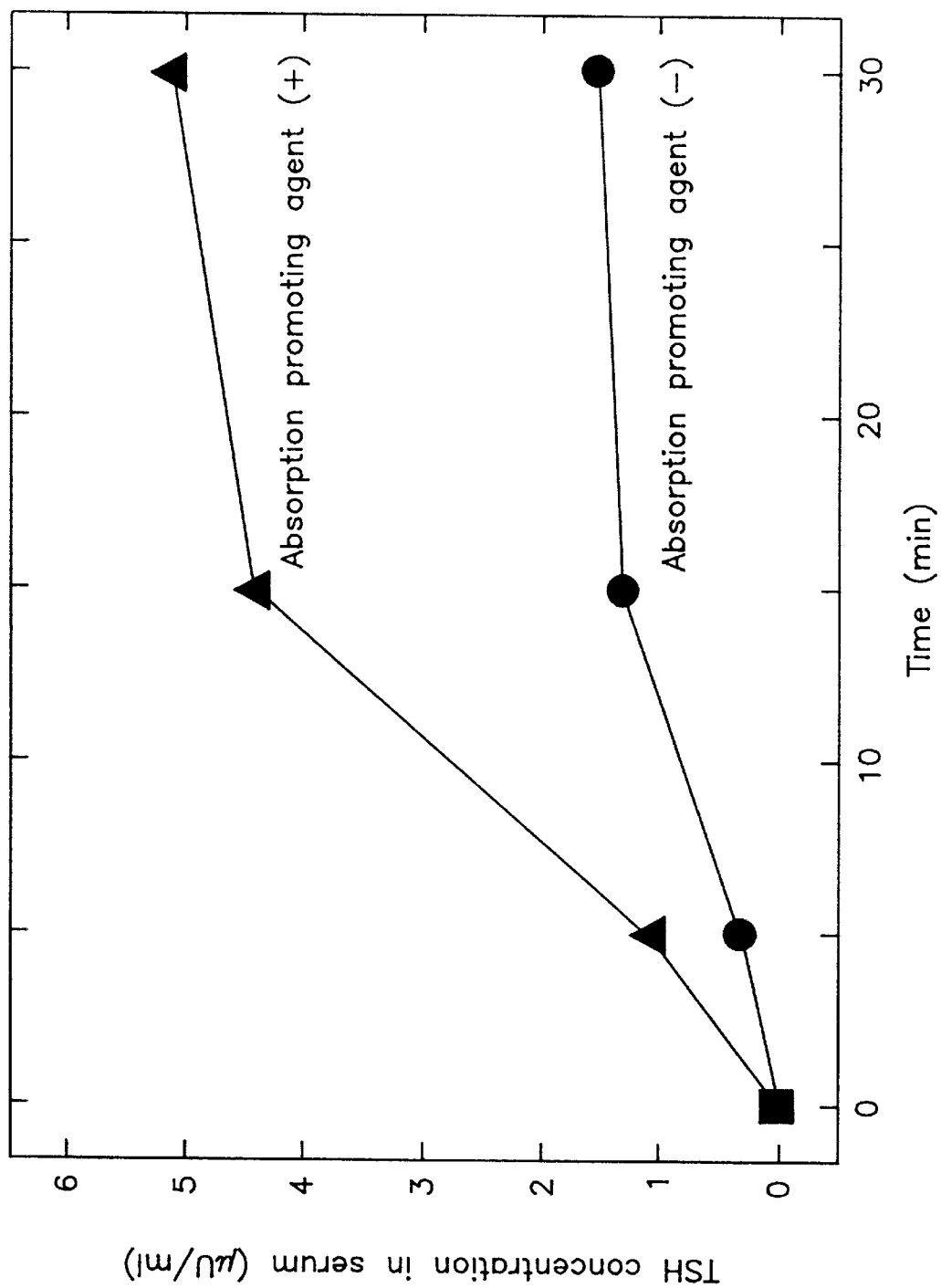
FIG. 5 is a graph showing the effects for promoting absorption of a thyroid-stimulating hormone by a combination of sucrose stearate and tartaric acid.

As is shown in FIG. 5, the solution of the invention showed far higher increase of the blood TSH concentration than the reference solution containing no absorption promoting agent.

EXPERIMENT 6

Effects for Promoting Absorption of ACTH

A solution containing BSA 0.3 w/v %, an absorption promoting agent (a combination of tartaric acid 1.0 w/v % and sucrose palmitate (P-1670) 0.5 w/v %) and ACTH 500 μg/ml was prepared. As a reference solution, there was prepared a solution containing BSA 0.3 w/v % and ACTH 500 μg/ml.

In the same manner as described in Experiment 1, the test solution was administered to the rats in an amount of ACTH 100 μg per each rat and the blood was collected at intervals. After the serum was separated, the blood ACTH concentration was measured by RIA. The results are shown in the accompanying FIG. 6.

Figure 6:
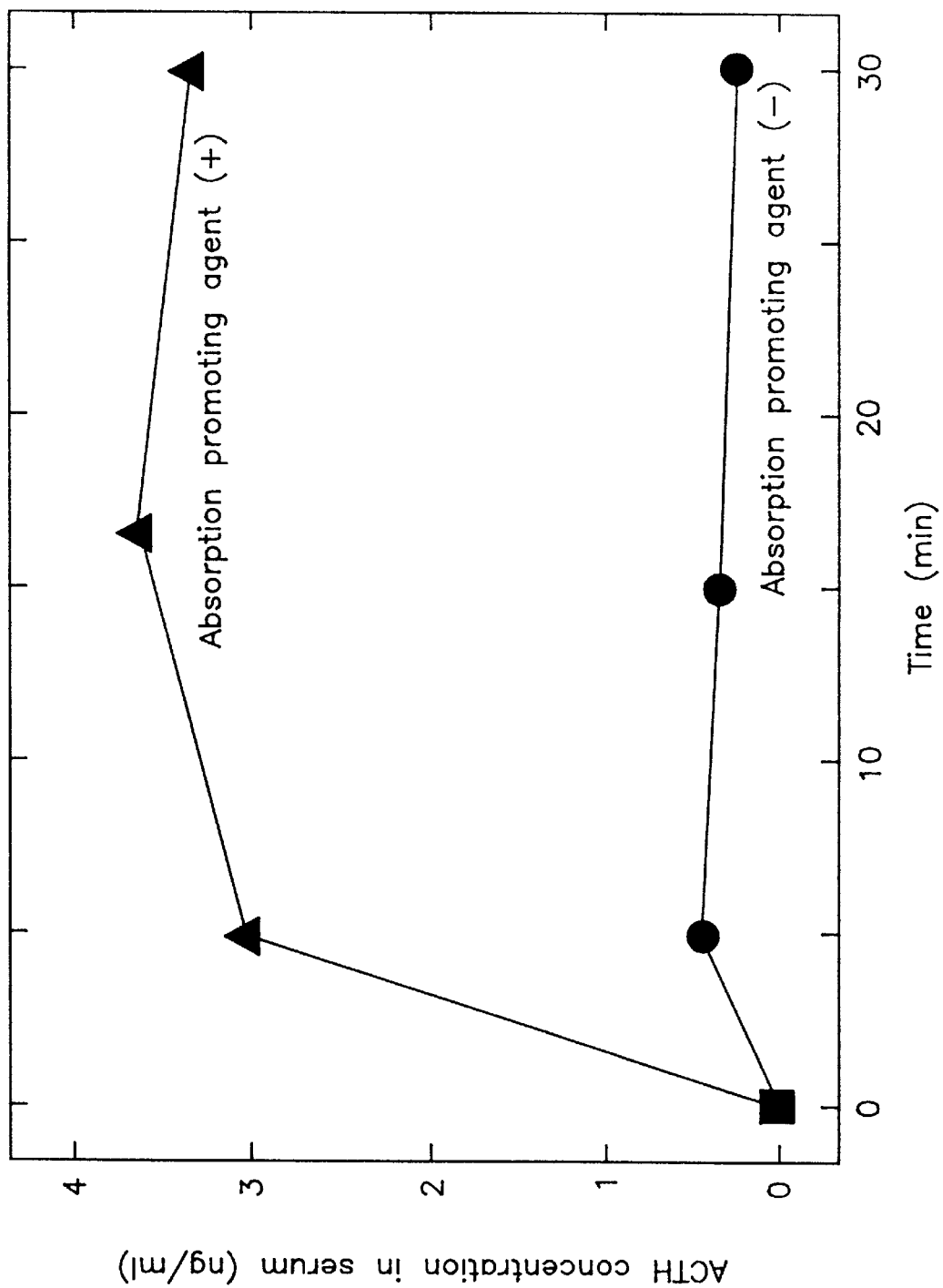
FIG. 6 is a graph showing the effects for promoting absorption of an adrenocorticotrophic hormone by a combination of sucrose palmitate and tartaric acid.

As is shown in FIG. 6, the solution using an absorption promoting agent of the invention showed far higher increase of the blood ACTH concentration than the reference solution containing no absorption promoting agent.

EXAMPLE 1

Tablets

In accordance with the tablet formulation as shown in Table 2, lactose, corn starch, tartaric acid, a fatty acid sucrose ester (Ryoto Sugar Ester L-1695, manufactured by Mitsubishi Chemical, Japan), h-CT and BSA are mixed, and thereto is added an aqueous solution of hydroxypropyl cellulose (HPC). The mixture is kneaded and extruded to granulate to give granules. The granules are mixed with magnesium stearate, and the mixture is tableted with a tableting machine to give crude tablets (each diameter 8 mm, weight 250 mg).

TABLE 2

| Tablet components | Amount |
|---|---|
| Lactose | 22.8 g |
| Corn starch | 21.0 g |
| Fatty acid sucrose ester | 1.5 g |
| Tartaric acid | 3.0 g |
| Human calcitonin (h-CT) | 0.1 g |
| Bovine serum albumin (BSA) | 0.3 g |
| Hydroxypropyl cellulose (HPC) | 1.2 g |
| Magnesium stearate | 0.1 g |

The crude tablets thus prepared are coated with a coating liquid prepared according to the coating formulation as shown in Table 3 with a high coater to give the desired tablets.

TABLE 3

| Coating formulation | Amount |
|---|---|
| Hydroxypropyl methyl cellulose acetate succinate | 10 g |
| Triethyl citrate | 2 g |
| Ethanol | 80 g |
| Water | 8 g |

EXAMPLE 2

Capsules

In accordance with the capsule formulation as shown in Table 4, malic acid, a fatty acid sucrose ester (Ryoto Sugar Ester L-1695, manufactured by Mitsubishi Chemical, Japan), salmon calcitonin and BSA are mixed, and the mixture (each 100 mg) is filled into Japan Pharmacopeia #4 capsule to give capsules.

TABLE 4

| Capsule components | Amount |
|---|---|
| Malic acid | 12.4 g |
| Fatty acid sucrose ester | 6.0 g |
| Salmon calcitonin | 0.4 g |
| Bovine serum albumin (BSA) | 1.2 g |

The capsules thus prepared are coated with a coating liquid prepared according to the coating formulation as shown in Table 5 with a fluidized granulator to give the desired capsules.

TABLE 5

| Coating formulation | Amount |
|---|---|
| Methacrylic copolymer-S | 20 g |
| Castor oil | 3 g |
| Ethanol | 377 g |

EXAMPLE 3

Granules

In accordance with the granule formulation as shown in Table 6, lactose, corn starch, human calcitonin, BSA, citric acid and a fatty acid sucrose ester are mixed, and thereto is added an aqueous solution of HPC. The mixture is kneaded and extruded to granulate to give granules.

TABLE 6

| Granule components | Amount |
|---|---|
| Lactose | 7.2 g |
| Corn starch | 12.3 g |
| Human calcitonin | 0.2 g |
| Bovine serum albumin (BSA) | 0.6 g |
| Citric acid | 6.2 g |
| Fatty acid sucrose ester | 3.0 g |
| Hydroxypropyl cellulose (HPC) | 0.5 g |

The granules thus prepared are film-coated with a coating liquid prepared according to the coating formulation as shown in Table 7 with a fluidized granulator to give the desired granules.

TABLE 7

| Coating formulation | Amount |
|---|---|
| Methacrylic copolymer-S | 30 g |
| Castor Oil | 1.5 g |
| Talc | 15 g |
| Ethanol | 498 g |
| Purified water | 55.5 g |

EXAMPLE 4

Sublingual Tablets

In accordance with the formulation as shown in Table 8, lactose, corn starch, hydroxypropyl cellulose, sucrose stearate, tartaric acid, and human calcitonin are mixed, and the mixture is tableted with a tableting machine to give the desired sublingual tablets.

TABLE 8

| Sublingual tablet components | Amount |
| --- | --- |
| Lactose | 75.6 g |
| Corn starch | 13 g |
| Hydroxypropyl cellulose | 1 g |
| Sucrose stearate | 3 g |
| Tartaric acid | 7 g |
| Human calcitonin (h-CT) | 0.4 g |

EXAMPLE 5

Sublingual Tablets

In accordance with the formulation as shown in Table 9, the desired sublingual tablets are prepared in the same manner as described in Example 4.

TABLE 9

| Sublingual tablet components | Amount |
| --- | --- |
| Lactose | 58.8 g |
| Crystalline cellulose | 24 g |
| Polyvinylpyrrolidone | 3 g |
| Sucrose palmitate | 4 g |
| Malic acid | 10 g |
| Human calcitonin (h-CT) | 0.2 g |

EXAMPLE 6

Sublingual Tablets

In accordance with the formulation as shown in Table 10, the desired sublingual tablets are prepared in the same manner as described in Example 4.

TABLE 10

| Sublingual tablet components | Amount |
| --- | --- |
| Lactose | 67 g |
| Sorbitol | 4 g |
| Mannitol | 8.4 g |
| Carboxymethyl cellulose sodium | 2.6 g |
| Sucrose oleate | 5 g |
| Citric acid | 12 g |
| Salmon calcitonin | 1 g |

EXPERIMENT 7

Effects for promoting absorption of calcitonin in sublingual tablets:

The sublingual tablets prepared as in Examples 4 and 5 were used as the test material (content of calcitonin, 1 mg or 0.5 mg per each tablet, 250 mg).

Figure 7:
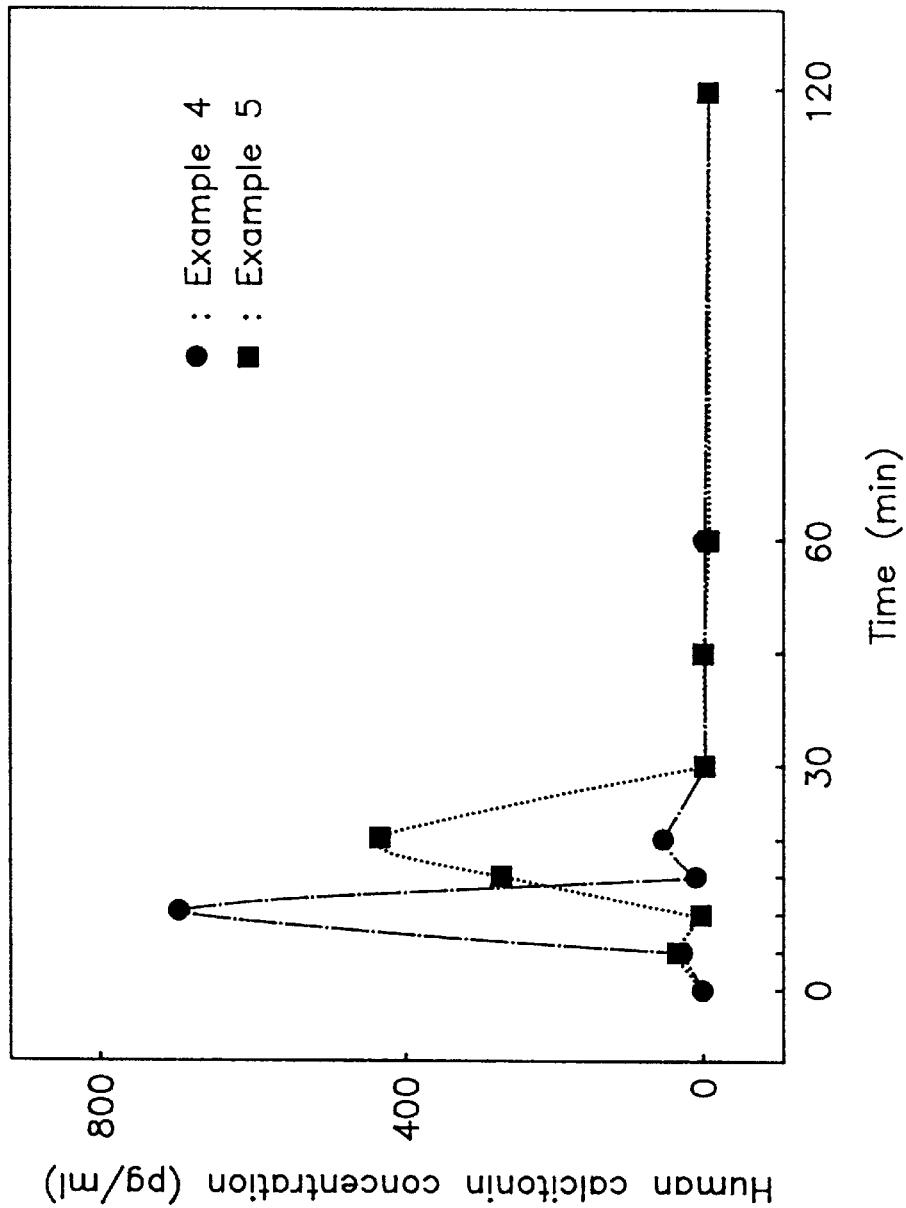
FIG. 7 is a graph showing the effects for promoting absorption of calcitonin in a sublingual tablet.

The test material (each one tablet) was administered by a sublingual route to a male Beagle dog which fasted overnight. After the administration, the blood was collected at intervals (after 5, 10, 15, 20, 30, 45, 60 and 120 minutes). After the serum was separated, the blood human calcitonin concentration was measured by RIA. The results are shown in the accompanying FIG. 7.

EXAMPLE 7

Rapidly Soluble Preparation

In accordance with the formulation as shown in Table 11, salmon calcitonin 10 mg, tartaric acid 2 g, and sucrose stearate 1 g are dissolved in an aqueous gelatin solution (1 w/v %) 10 ml. The solution (each 1 ml) is added to a vessel, followed by lyophilization to give the desired rapidly soluble preparation (sublingual tablets).

TABLE 11

| Raidly soluble prepar. components | Amount |
| --- | --- |
| Aqueous gelatin solution (1 w/v %) | 10 ml |
| Tartaric acid | 2 g |
| Sucrose stearate | 1 g |
| Salmon calcitonin | 10 mg |

EXAMPLE 8

Rapidly Soluble Preparation

In accordance with the formulation as shown in Table 12, the desired rapidly soluble preparation (sublingual tablets) is prepared in the same manner as described in

EXAMPLE 7.

TABLE 12

| Raidly soluble prepar. components | Amount |
| --- | --- |
| Aqueous gelatin solution (1 w/v %) | 10 ml |
| Citric acid | 1 g |
| Sucrose oleate | 0.2 g |
| Human calcitonin | 10 mg |

EXPERIMENT 8

Effects for promoting absorption of calcitonin by using a combination of various organic acids and a fatty acid sucrose ester in rapidly soluble composition:

Test materials were prepared by dissolving salmon calcitonin 3 mg, an organic acid 20 w/v %, and sucrose stearate (S-970) 10 w/v % to a 1 w/v % aqueous gelatin solution 3 ml, adding the solution (each 1 ml) to a vessel, followed by lyophilization.

Each one of the test material was administered by a sublingual route to a male Beagle dog which fasted overnight, and the blood was collected at intervals (after 10, 20, 30, 45 and 60 minutes). After the serum was separated, the calcium concentration in serum was measured with Calcium C kit (manufactured by Wako Junyaku K. K., Japan) (n=3). The results are shown in Table 13.

As is shown in Table 13, in each material using any organic acid, there was observed the lowering of blood calcium concentration, while no lowering of blood calcium concentration was observed in the material using no organic acid.

TABLE 13

[Lowering rate of serum calcium (%)]

| | Time after administration (min) | | | | |
| --- | --- | --- | --- | --- | --- |
| organic acids | 10 | 20 | 30 | 45 | 60 |
| Tartaric acid | 3.0 | 2.9 | 5.1 | 8.3 | 7.8 |
| Citric acid | 4.5 | 2.3 | 3.0 | 1.6 | 2.2 |
| Malic acid | 4.5 | 2.7 | 3.3 | 1.4 | 1.5 |
| (−) | −2.2 | −1.5 | −3.6 | −3.1 | −4.1 |

EXPERIMENT 9

Effects for promoting absorption of an active substance by using fatty acid sucrose esters having different HLB values in rapidly soluble composition:

Test materials were prepared by dissolving salmon calcitonin 3 mg, tartaric acid 20 w/v %, and each fatty acid sucrose ester 10 w/v % to a 1 w/v % aqueous gelatin solution 3 ml, adding the solution (each 1 ml) to a vessel, followed by lyophilization.

In the same manner as described in Experiment 8, the test material was administered to the dog, and the blood was collected at intervals, and the blood calcium concentration was measured. The results are shown in Table 14.

As is shown in Table 14, in each material using fatty acid sucrose esters having various HLB values, there was observed the lowering of blood calcium concentration.

TABLE 14

[Lowering rate of serum calcium (%)]

| HLB values | Time after administration (min) | | | | |
|---|---|---|---|---|---|
| | 10 | 20 | 30 | 45 | 60 |
| 9 | 3.0 | 2.9 | 5.1 | 8.3 | 7.8 |
| 5 | 3.0 | 7.5 | 4.1 | 8.6 | 6.1 |
| 3 | 4.7 | 3.3 | 3.2 | 2.8 | 3.6 |

EXPERIMENT 10

Effects of the concentration of an organic acid and a fatty acid sucrose ester on the absorption of the active ingredient in rapidly soluble composition:

Test materials were prepared by dissolving human calcitonin 3 mg, citric acid and sucrose stearate (S-970) in the concentration as shown in Table 15 to a 1 w/v % aqueous gelatin solution 3 ml, adding the solution (each 1 ml) to a vessel, followed by lyophilization.

In the same manner as in Experiment 8, the test material was administered to the dog, and the blood was collected at intervals. After the serum was separated, the human calcitonin concentration in serum was measured by RIA. The results are shown in Table 15.

As is shown in Table 15, in the test materials of all concentrations of the organic acid and fatty acid sucrose ester, there was observed the absorption of human calcitonin, but the absorption promoting effect became weaker with lowering of the concentration of the absorption promoting agent.

TABLE 15

| Concentration of absorption promoting agents (w/v %) | | Maximum blood concentration of human calcitonin in average (pg/ml) |
|---|---|---|
| S-970 | Citric acid | |
| 10.0 | 20.0 | 1652 |
| 5.0 | 10.0 | 1116 |
| 2.5 | 5.0 | 191 |
| 1.0 | 2.0 | 86 |

EXPERIMENT 11

Effects for promoting absorption of calcitonin by using a combination of an organic acid and a fatty acid sucrose ester in rapidly soluble composition:

Test materials were prepared by dissolving human calcitonin (h-CT) 3 mg, tartaric acid 10 w/v %, and sucrose stearate (S-570) 2 w/v % to a 1 w/v % aqueous gelatin solution 3 ml, adding the solution (each 1 ml) to a vessel, followed by lyophilization.

In the same manner as described in Experiment 8, the test material was administered to the dog, and the blood was collected at intervals. After the serum was separated, there were measured the blood calcium concentration with Calcium C kit (manufactured by Wako Junyaku K. K., Japan), the blood phosphur concentration with Phosphur-C Test (manufactured by Wako Junyaku K. K., Japan), and the blood human calcitonin concentration by RIA. The results are shown in the accompanying FIG. 8.

Figure 8:
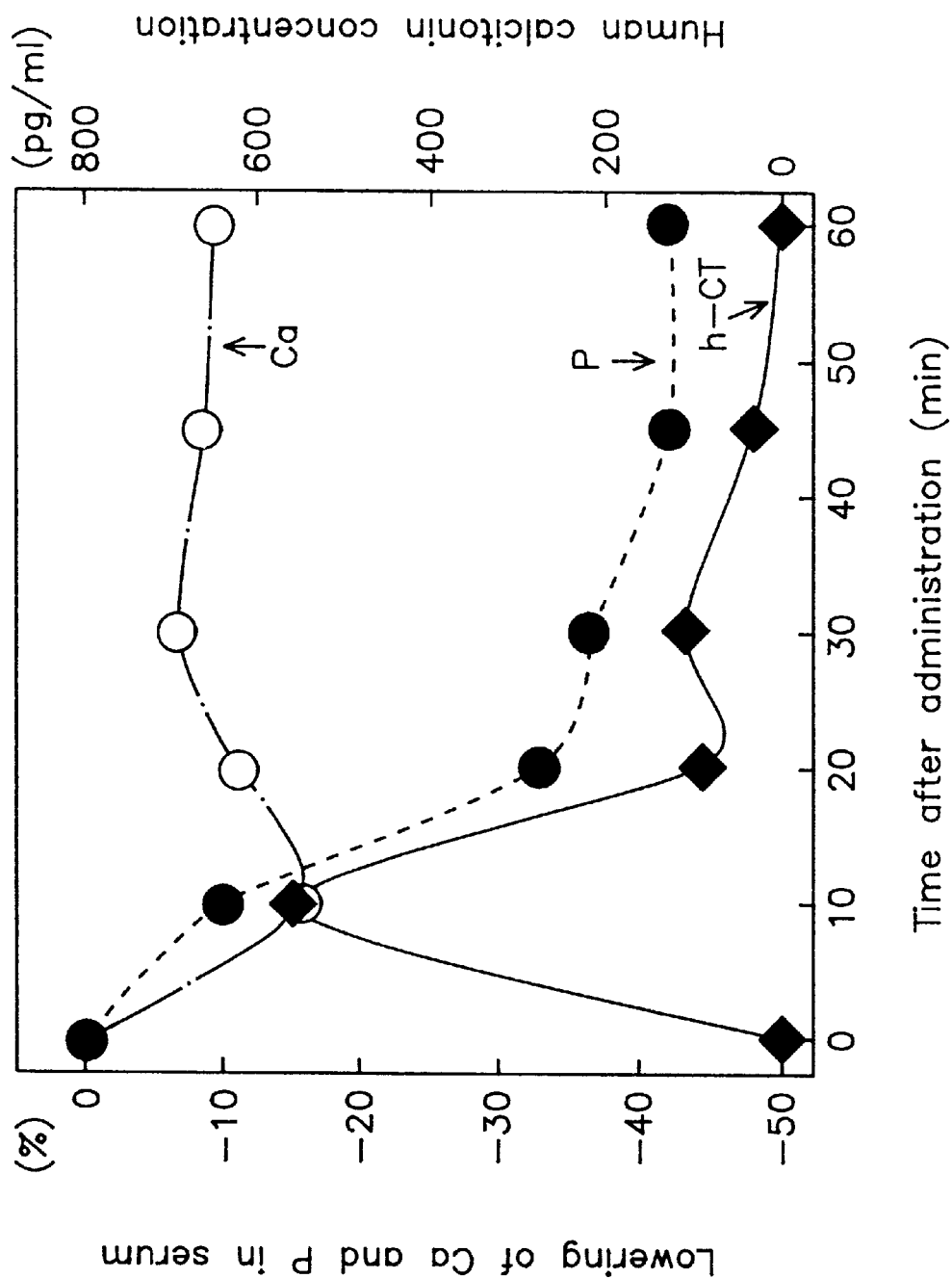
FIG. 8 is a graph showing the effects for promoting absorption of calcitonin by a combination of various fatty acid sucrose esters and tartaric acid in a rapidly soluble composition.

As is shown in FIG. 8, with increase of the blood human calcitonin, the concentrations of calcium and phosphur in blood were lowered.

Effects of the Invention

When polypeptide hormones are administered orally, they are usually decomposed by a protease and hence are insufficiently absorbed and can not exhibit their sufficient physiological activities. From this viewpoint, the polypeptide hormones are usually administered by injection. On the contrary, according to the composition incorporated by an absorption promoting agent of the present invention, the polypeptide hormones can highly be absorbed through the intestinal tract and the membrane within the oral cavity, and thereby, the hormones can exhibit their physiological activities even by oral administration or by application into the oral cavity.

What is claimed is:

1. A method for promoting the absorption of a physiologically active polypeptide which is calcitonin, which comprises administering said polypeptide to a patient via oral or sublingual administration in combination with:

(1) an absorption promoting agent consisting of (i) an organic acid selected from the group consisting of acetic acid, butyric acid, fumaric acid, malonic acid, phthalic acid, propionic acid, glutaric acid, adipic acid, valeric acid, caproic acid, maleic acid, ascorbic acid, isoascorbic acid, malic acid, succinic acid, lactic acid, tartaric acid, citric acid, benzoic acid, pharmaceutically acceptable salts thereof, or a combination of one or more thereof, and (ii) a fatty acid sucrose ester; and (2) a pharmaceutically acceptable carrier or diluent.

2. The method according to claim 1, wherein the composition is administered orally.

3. A method for promoting the absorption of a physiologically active polypeptide, which comprises administering said polypeptide to a patient via oral or sublingual administration in combination with:

(1) an absorption promoting agent consisting of (i) an organic acid selected from the group consisting of malic acid, succinic acid, lactic acid, tartric acid, citric acid, benzoic acid, pharmaceutically acceptable salts thereof, or a combination of one or more thereof, and (ii) a fatty acid sucrose ester selected from the group consisting of sucrose stearate, sucrose palmitate, sucrose oleate and sucrose laurate; and (2) a pharmaceutically acceptable carrier or diluent.

4. The method according to claim 3, wherein the polypeptide is calcitonin.

5. The method according to claim 3, wherein the composition is administered orally.

* * * * *